United States Patent
Heller et al.

(10) Patent No.: US 6,623,501 B2
(45) Date of Patent: Sep. 23, 2003

(54) REUSABLE CERAMIC SKIN-PIERCING DEVICE

(75) Inventors: Adam Heller, Austin, TX (US); James L. Say, Alameda, CA (US); Jeffery V. Funderburk, Fremont, CA (US)

(73) Assignee: TheraSense, Inc., Alameda, CA (US)

( * ) Notice: Subject to any disclaimer, the term of this patent is extended or adjusted under 35 U.S.C. 154(b) by 0 days.

(21) Appl. No.: 09/827,109

(22) Filed: Apr. 5, 2001

(65) Prior Publication Data

US 2001/0041904 A1 Nov. 15, 2001

Related U.S. Application Data

(60) Provisional application No. 60/194,733, filed on Apr. 5, 2000, and provisional application No. 60/196,217, filed on Apr. 11, 2000.

(51) Int. Cl.[7] .............................................. A61B 17/32
(52) U.S. Cl. ...................................... 606/181; 606/167
(58) Field of Search .............................. 606/45, 49, 1, 606/181–185, 167, 171, 172; 600/583, 573, 584, 576, 578

(56) References Cited

U.S. PATENT DOCUMENTS

| | | | |
|---|---|---|---|
| 3,762,243 A | * 10/1973 | Borrkfield | 205/122 |
| 4,307,984 A | * 12/1981 | Patterson | 125/39 |
| 4,850,353 A | * 7/1989 | Stasz et al. | 606/39 |
| 5,071,418 A | * 12/1991 | Rosenbaum | 606/42 |
| 5,529,581 A | 6/1996 | Cusack | |
| 5,554,153 A | 9/1996 | Costello et al. | |
| 5,868,772 A | 2/1999 | LeVaughn et al. | |
| 6,027,459 A | 2/2000 | Shain et al. | |
| 6,126,656 A | * 10/2000 | Billings | 606/41 |
| 6,156,051 A | 12/2000 | Schraga | |
| 6,183,489 B1 | 2/2001 | Douglas et al. | |
| 6,258,086 B1 | * 7/2001 | Ashley et al. | 606/41 |
| 6,327,784 B1 | * 12/2001 | Altena et al. | 30/346.53 |

* cited by examiner

Primary Examiner—Michael J. Milano
Assistant Examiner—Jessica R. Baxter
(74) Attorney, Agent, or Firm—Merchant & Gould P.C.

(57) ABSTRACT

A reusable ceramic skin-piercing device. The skin-piercing device is capable of piercing the skin so as to make a sample of biological fluid available for an assay. In one embodiment, the skin-piercing device includes a skin-piercing element which is heated prior to use to a sufficiently high temperature to kill or deactivate pathogenic microorganisms. The device is heat-sterilized, being heated by passing an electrical current through a resistive element in thermal contact with the heat-conducting ceramic piercer. In another embodiment, the skin-piercing device includes a sleeve of elastomeric material with a sterilizing agent disposed in contact with the skin-piercing element. The sterilizing agent sterilizes the skin-piercing element after use.

The skin-piercing element is made of a hard refractory ceramic material. The ceramic material is optionally a composite, for example, a composite of a ceramic material and a metal, or multiple ceramic materials.

7 Claims, 4 Drawing Sheets

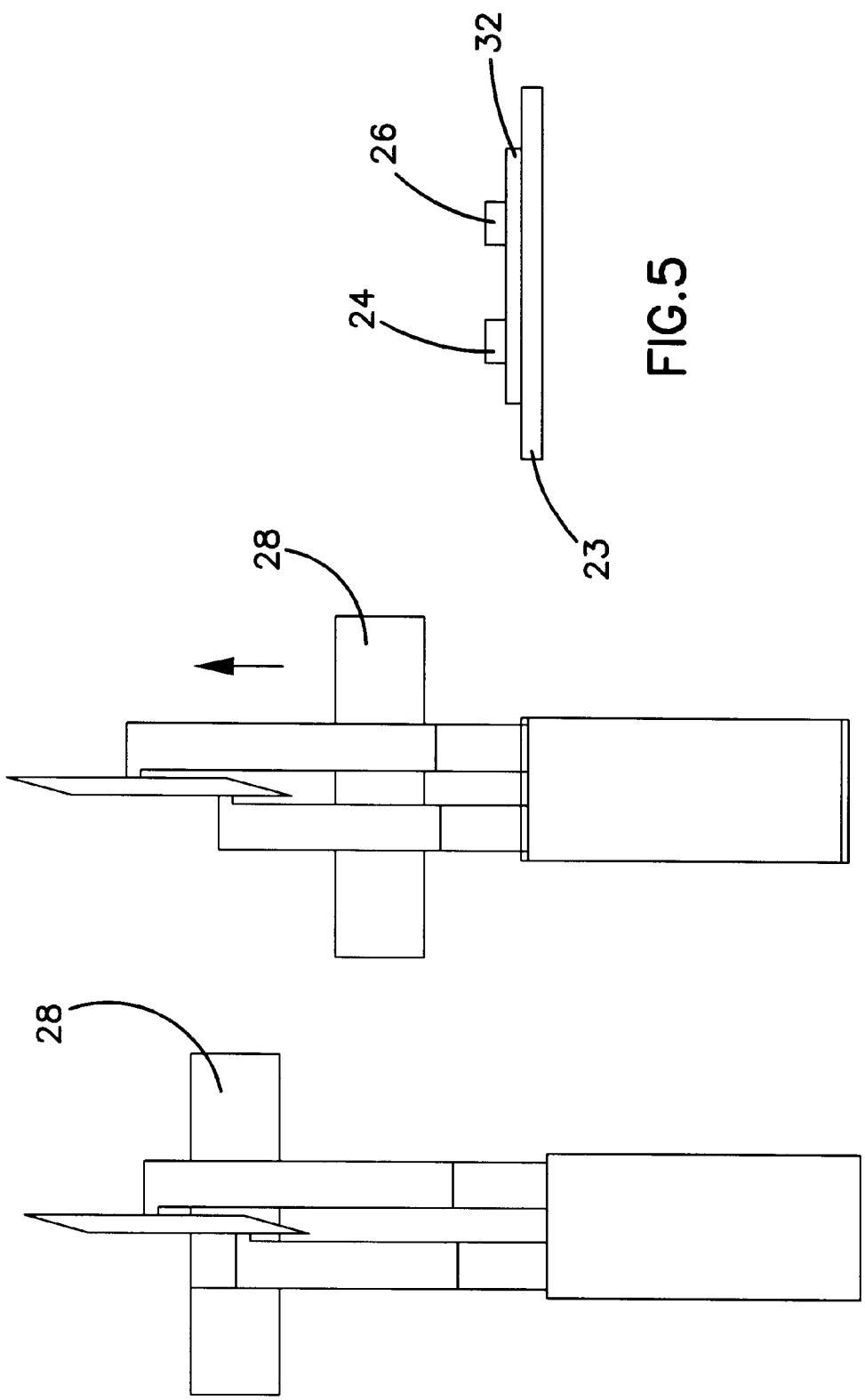

REUSABLE CERAMIC SKIN-PIERCING DEVICE

This application claims the benefit of U.S. Provisional Application Serial No. 60/194,733 filed Apr. 5, 2000 and U.S. Provisional Application Serial No. 60/196,217 filed Apr. 11, 2000.

FIELD OF THE INVENTION

This invention relates generally to skin-piercing devices and methods, and in particular, to reusable skin-piercing devices and methods, where the reusable skin piecing device is heat-sterilized prior to reuse.

BACKGROUND OF THE INVENTION

Diabetic people use lancets to pierce their skin in order to obtain small samples of blood for electrochemical, photonic or other glucose assays. The lancets commonly used are made of steel. Even though it is recommended that they be used only once, while the lancets are still sterile, many diabetic people use them multiple times to lower the cost of monitoring their glycemia (by measuring blood glucose concentration).

There are several problems with using the lancet more than once. For example, after its first use the lancet device is no longer sterile. Also, when used more than once, the point of the lancet is blunted. After a few piercings with the lancet, the lancet no longer punctures the skin. Therefore, the skin area impacted by the tip of the lancet increases, and the force driving the lancet through the skin must be increased. With the increase of force and of the pierced area, the pain associated with obtaining the sample becomes greater. In addition, the spatial definition, i.e., the accuracy of the placement in the pierced zone of the skin relative to an object that is part of the glucose assaying system, degrades when the tip is blunted.

SUMMARY OF THE INVENTION

In accordance with the present invention, the above and other problems are solved by providing a reusable ceramic skin-piercing device and method. The skin-piercing device is capable of piercing the skin so as to make a sample of biological fluid available for an assay, and includes a skin-piercing element which is heated prior to use to a sufficiently high temperature to deactivate or kill pathogenic microorganisms. The device is heat-sterilized, being heated by passing an electrical current through a resistive region in thermal contact with the heat-conducting ceramic skin-piercing device. The device is used to obtain a small, usually less than 5 $\mu$L, sample of blood or of subcutaneous fluid for an assay, particularly of glucose.

Another embodiment of the invention is a skin-piercing device having a skin-piercing element that includes a blade (e.g., a ceramic blade) and a sleeve disposed around the skin-piercing element. The sleeve includes an elastomeric material and a sterilizing agent. The sterilizing agent sterilizes the skin-piercing element after use.

The skin-piercing element is made of a hard refractory ceramic material. In another embodiment, the ceramic material may be a composite, for example, a composite of a ceramic material and a metal, or of multiple ceramic materials.

BRIEF DESCRIPTION OF THE DRAWINGS

FIG. 3 illustrates a top plan view of one embodiment of a reusable skin-piercing device with a heat sink placed proximate a non-cutting end of a ceramic blade, according to the invention;

FIG. 4 illustrates a top plan view of another embodiment of a reusable skin-piercing device with a heat sink placed between the ceramic blade and a electrical circuitry, according to the invention;

FIG. 5 illustrates a partial cross-sectional view of an embodiment of a reusable skin-piercing device, according to the present invention;

Figure 1:
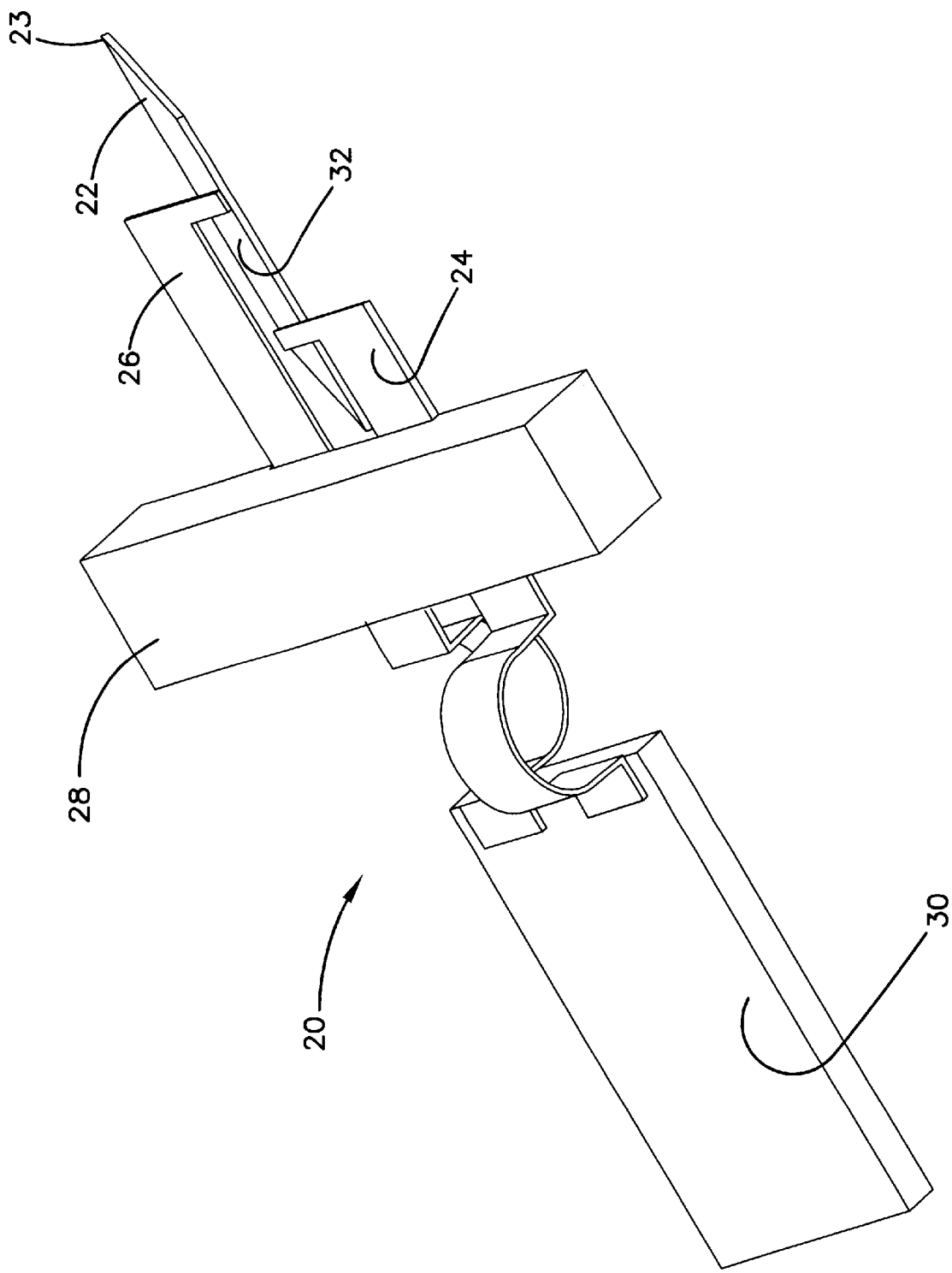
FIG. 1 illustrates a front perspective view of the components of one embodiment of a reusable skin-piercing device, according to the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to skin-piercing devices, such as lancets, and methods of using skin-piercing devices. In particular, the present invention is directed to reusable ceramic skin-piercing devices and methods of using these devices. While the present invention is not so limited, an appreciation of various aspects of the invention will be gained through a discussion of the examples provided below.

Heat Sterilization

Figure 2:
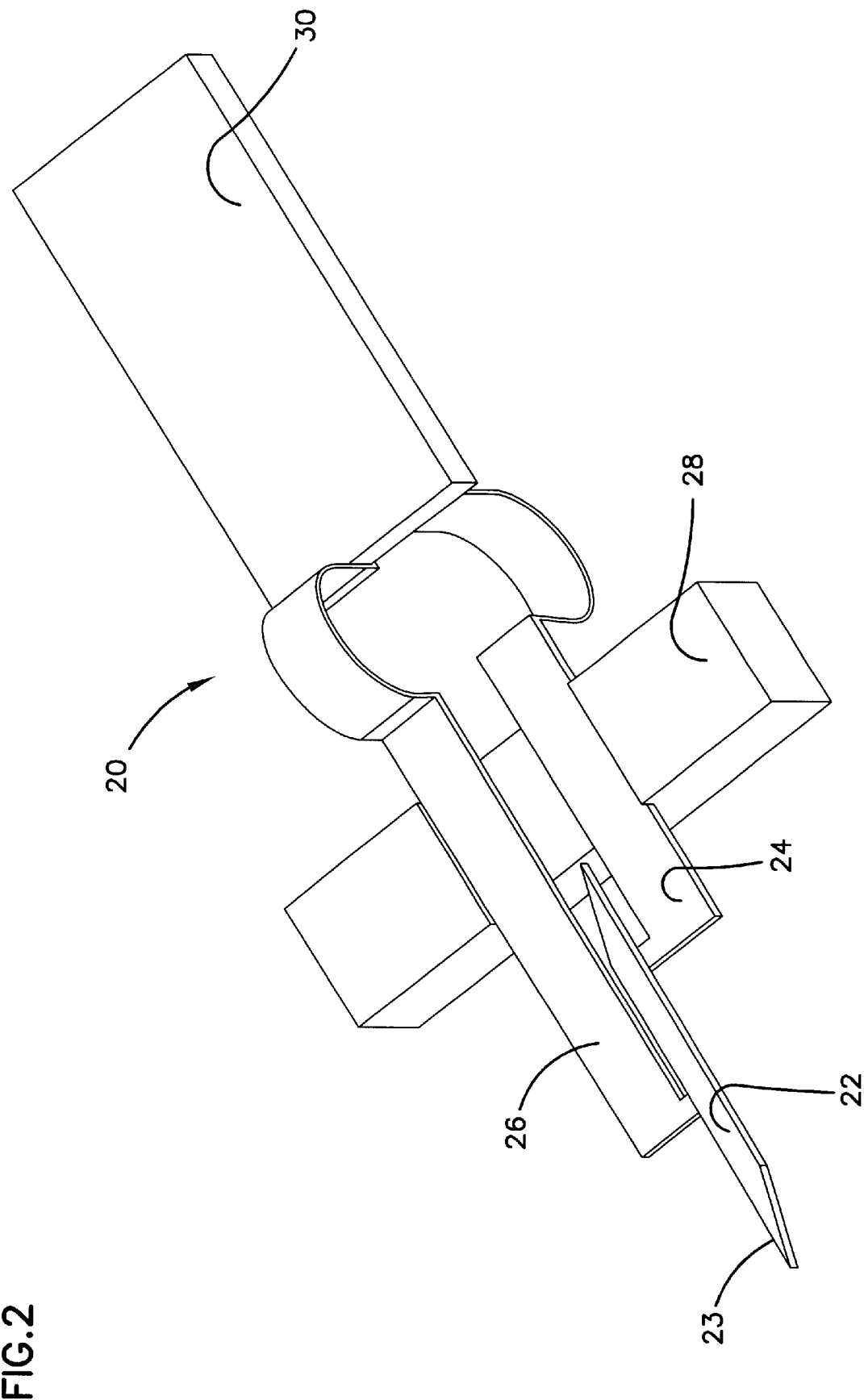
FIG. 2 illustrates a back perspective view of the reusable skin-piercing device of FIG. 1.

Referring now to FIGS. 1 and 2, which illustrate the components of one embodiment of a skin-piercing device, shown generally as 20. The skin-piercing device includes a skin-piercing element 22, including a ceramic blade 23 and a resistive region 32, two conductors 26, 24, an optional heat sink 28, and circuitry 30 to provide current between the two conductors to heat the skin-piercing element. All of these components are typically contained within a housing (not shown).

In use, the device is heat sterilized prior to its reuse. The heat is generated by passage of an electrical current through the resistive region 32, which is in thermal contact with the ceramic blade 23. The current can be a direct current or an alternating current.

The skin-piercing element 22 can include a double-sided blade, as illustrated in FIG. 1. This allows the user to use the other blade when the first blade is no longer usable. A skin-piercing element with single-sided blade is also suitable.

The body of the skin-piercing element 22, and in particular, the ceramic blade 23, is typically made of a hard refractory ceramic material. In some embodiments, the ceramic material is a composite, for example, a composite of a ceramic material and a metal, or a composite of multiple ceramic materials.

The ceramic material is hard, so as to reduce its wear upon piercing of the skin. The hardness of the material typically exceeds that of easily machined steels, such as, for example, Martensite with 0.7% carbon which has a Brinnell hardness number of about 700 and a Rockwell hardness of about 63 HRG. The hardness of the ceramic material preferably equals or exceeds the hardness of crystalline quartz, which is about 800 on the Knoop hardness scale, about 7 on the Mohs hardness scale, and about 600 on the Brinnell hardness scale as described on page 139 of the book "Materials Science and Engineering: An Introduction" by William D. Callister, Second Edition, Wiley New York, 1985. Such materials include, for example, a number of crystalline oxides, nitrides, borides, and carbides, as well as diamond. Diamond refers to a material in which the carbon-carbon bonds are tetrahedral and in which a small fraction of the bonds, up to about 1 in 50, can optionally be carbon-hydrogen or carbon-fluorine bonds.

The ceramic material can be monocrystalline or polycrystalline. If the ceramic material is polycrystalline its density is typically greater than 96% of the theoretical (i.e., the density of a monocrystalline material). Preferably its density is greater than 98% of the theoretical, and it is most preferable if its density is 99% of the theoretical or greater.

Examples of suitable crystalline oxides are the oxides of aluminum, such as sapphire and corundum. These are rated at about 9 on the Mohs hardness scale. Spinel, $MgAl_2O_4$, and cubic zirconia are examples of other suitable crystalline oxides, as well as topaz which has a hardness of about 8 on the Mohs scale. Examples of suitable polycrystalline oxides are alumina, alumina-zirconia alloys, and zirconia, stabilized or partially stabilized, for example, with CaO. Examples of suitable nitrides include aluminum nitride (AlN), boron nitride (BN), silicon nitride ($Si_3N_4$), and the electrically conductive titanium nitride (TiN). Examples of suitable carbides include silicon carbide (SiC), boron carbide ($B_4C$), and the electrically conductive carbides of tungsten (e.g., WC), tantalum (e.g., TaC) and titanium (e.g., TiC). As is well known in the machine tool industry, crystallites of the hard metal carbides, borides and nitrides can be bound with a metal like cobalt to form an electrically conducting composite. The skin-piercing element may also be made of such a composite.

The tensile strength of suitable ceramic materials is generally at least about 172 MPa or 25 kpsi; preferably at least about 35 kpsi; more preferably at least about 60 kpsi; and most preferably at least about 70 kpsi. The flexural strength of a 20×40 mm sample of a suitable ceramic material is typically at least 45 kpsi; preferably at least 60 kpsi; more preferably at least 75 kpsi; and most preferably at least 80 kpsi. A suitable ceramic material's toughness or resistance to fracture in units of $kpsi.in^{0.5}$ is generally at least about 3.5. It is typically desirable for the toughness or resistance to be at least about 3.5, preferably at least about 5.

The thermal conductivity of suitable ceramic materials at 25° C. in units of $W\ m^{-1}\ (°\ K.)^{-1}$ is generally at least 2. It is typically desirable for the thermal conductivity to be greater than 2, preferably 30 or greater. Ceramic materials with a linear thermal expansion coefficient of no more than about $10^{-5}$ in the 25–700° C. temperature range are generally preferred. The preferred ceramic materials also do not absorb substantial amounts of water, as an example, a 1 cm×1 cm×0.1 cm slab of the preferred ceramic material does not absorb more than 0.03 wt. %, based on the weight of the slab, under operational conditions.

The thermal conductivity of the ceramic material is sufficiently high for the temperature of all surfaces of the skin-piercing element 22 to reach the sterilizing temperature when a non-penetrating part, or only one of the skin-piercing element 22 surfaces, is heated. The tensile strength and modulus of rupture of the ceramic material are selected to assure that the element will not break at the stress required to pierce the skin.

The resistive region is typically a metal or a semiconductor. When it is a semiconductor, it typically has a band gap smaller than 1 eV or highly doped and degenerate. The metal or semiconductor is typically refractory, meaning that it melts at a high temperature, generally at least about 1000° C. Metals or semiconductors melting at a temperature of at least about 1500° C. are preferred; more preferred are metals or semiconductors melting at a temperature of at least about 2000° C.

The skin-piercing element 22 can be formed in a number of ways to include a ceramic blade 23 and a resistive region 32. In one embodiment, illustrated in FIG. 5, the ceramic blade 23 is made using an electrically insulating ceramic material. The resistive region 32 is a resistive film formed on the ceramic blade 23. The films of the most preferred metal or semiconductor-comprising resistors adhere to the ceramic. The group of the most preferred group of resistor-materials include tungsten, molybdenum, tantalum, niobium or a platinum-group metal, such as ruthenium, platinum, palladium or rhodium. When the ceramic itself is the resistor, it can be a composite such as the tungsten carbide-cobalt composite used in machine tools. Any of the known film-forming methods can be used. These methods include, for example, evaporation, chemical or physical vapor deposition, sputtering, electroplating or electroless plating.

One method of forming the resistive film includes applying a precursor salt, such as, for example, a polytungstate, ammonium silicontungstate, or ammonium phosphotungstate, from an aqueous solution to the ceramic surface. The salt decomposes to fine-grained tungsten oxide when heated. This precursor oxide is then reduced to a resistive material by, for example, heating it in an atmosphere containing hydrogen or a hydrogen-precursor, such as $NH_3$, or by exposing the precursor oxide to a hydrogen-containing plasma. For example, the resistive film can be formed by applying a film comprising an electrically insulating oxide of tungsten to the ceramic oxide and reducing it in a hydrogen-containing atmosphere to a conductor, which typically includes metallic tungsten. The thickness and resistivity of the resistive film are selected to provide sufficient resistance to generate the necessary heating.

In an alternative embodiment, the ceramic blade 23 itself is made of an electrically conducting ceramic. In such instance, the current-conduction through the ceramic can be electronic, meaning electron or hole conduction, or ionic, as the case in certain oxides comprising aluminum, zirconium or thorium, or it can be both ionic and electronic.

The resistance of the resistive region (either a resistive film or the ceramic material itself) and separation between the conductors is selected to provide the necessary heating. As an example, the resistance of the resistive region between the conductors 24, 26 at 25° C. is typically not less than 0.001 ohms and is not greater than 100 ohms. The resistance preferably is in the range of 0.01 ohms to 10 ohms, more preferably in the range of 0.05 to 5 ohms, and most preferably in the range of 0.1 to 0.5 ohms.

Optionally, the skin-piercing element 22, particularly, the ceramic blade 23, is overcoated with a high-melting polymer film to which constituents of blood and skin do not adhere well. The preferred materials of these optional films comprise heat-stable silicones, such as silsesquioxanes formed, for example, from methyltrimethoxysilane, or fluorocarbon polymers (for example, polytetrafluoroethylene (e.g., Teflon™)), commonly applied in cookware, such as frying pans.

The two conductors 24, 26 are typically formed using a conductive material, such as conductive metals or conductive carbon. These two conductors 24, 26 are spaced apart from each other and are positioned to be in contact with a resistive region of the skin-piercing element 22. The conductors are preferably not rapidly oxidized in air at the sterilizing temperature, which is generally higher than 100° C. and is preferably 300° C. or higher. The conductors 24, 26 are selected to maintain conductivity after being heated multiple times to the temperature at which pathogenic viruses, bacteria and fungi are deactivated or killed.

The two conductors 24, 26 are connected to the circuitry 30 which produces a current between the two conductors to heat the skin-piercing element. The conductors can be directly or inductively coupled to the circuitry. The circuitry 30 can be of any known configuration. Typically, a user activates the circuitry 30 to begin the heating process prior to piercing the skin. Optionally, the circuitry 30 can be automatically activated when the skin-piercing element is retracted back into the housing after piercing the skin to deactivate or kill microscopic pathogenic viruses, bacteria and fungi. Generally, the time required to heat sterilize the skin-piercing element 22 is about 5 minutes or less, preferably, about 1 minute or less, more preferably, about 30 seconds or less, and can be as few as about 10 seconds or less. The length of time required generally depends on factors such as, for example, the resistivity of the resistive region 32, the distance between the conductors 24, 26, the amount of current flowing through the resistive region 32, and the thermal resistance of the skin-piercing element 22 (See FIG. 5).

The source of power for the circuitry is typically a battery (not shown), however other sources of power can be used. For example, in one embodiment, the skin-piercing device is portable and has one or more batteries providing an open circuit potential greater than 1 V DC. In another embodiment, the current source is a standard 110 VAC or 220 VAC 50 or 60 Hz source. The current source typically also includes a capacitor, the capacitance of which exceeds 100 microfarads, preferably exceeds 1 millifarad, and is most preferably about 10 millifarad. The circuit also includes a switch capable of carrying, when closed, at least 10 mA, preferably at least 100 mA, and more preferably about 1 A or more.

Optionally, the circuitry 30 or other mechanism in the device prevents cocking or activation of the skin-piercing device unless the skin-piercing element has been heated.

The ceramic skin-piercing device 20 optionally has a heat sink 28 to prevent excessive heating to areas of the device 20 where it is not required or desired. The heat sink is attached to the conductors 24, 26. As seen in FIG. 3, the heat sink 28 can be placed at the end of the ceramic blade not used for piercing the skin. In an alternative embodiment, the heat sink can be positioned elsewhere, such as in FIG. 4 (as well as FIGS. 1 and 2), where the heat sink 28 is placed between the ceramic blade 23 and the circuitry 30. The heat sink 28 is typically made of a material that readily absorbs and dissipates heat, however, the placement of the heat sink should be selected so that the ceramic blade of the skin-piercing element is adequately heated during the process.

The heating can be controlled or monitored by a heat sensor, such as a thermocouple, infrared sensitive or visible light sensitive photodiode, radiometer, bolometer, or a current sensor, or both. In an alternative embodiment, a timer can regulate the time that current is applied to the piercing element.

Typically a waiting period before use is not required. The device may be set up such that after a heating period, or a subsequent cooling period, the device will indicate it is ready for use. The device may also be set up such that the ceramic blade 23 is not able to be cocked into piercing position or released unless the device 20 has been sterilized and is ready for use. In an alternative embodiment, the skin-piercing element 22 retreats back into the housing after use, and triggers a heating cycle.

Non-heat Sterilization

Figure 7:
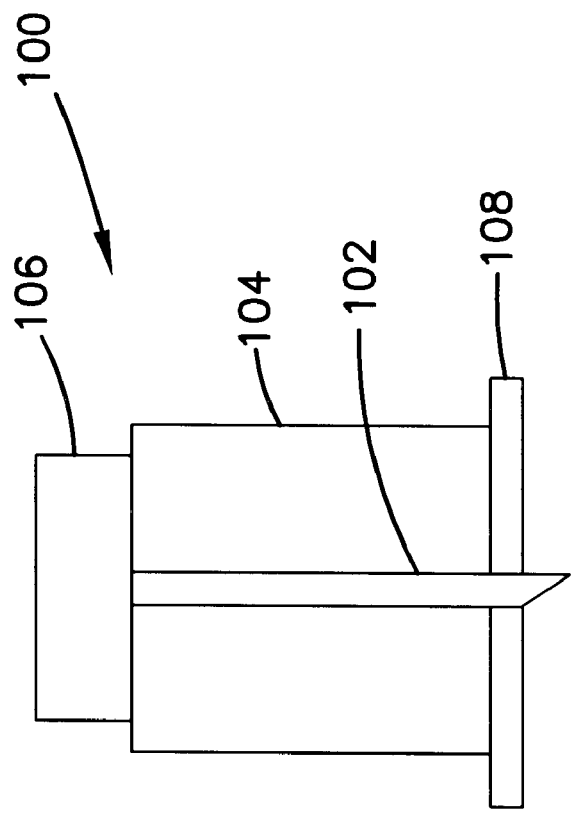
FIG. 7 is a schematic cross-sectional view of the device of FIG. 6 with a skin-piercing element extended.
Figure 6:
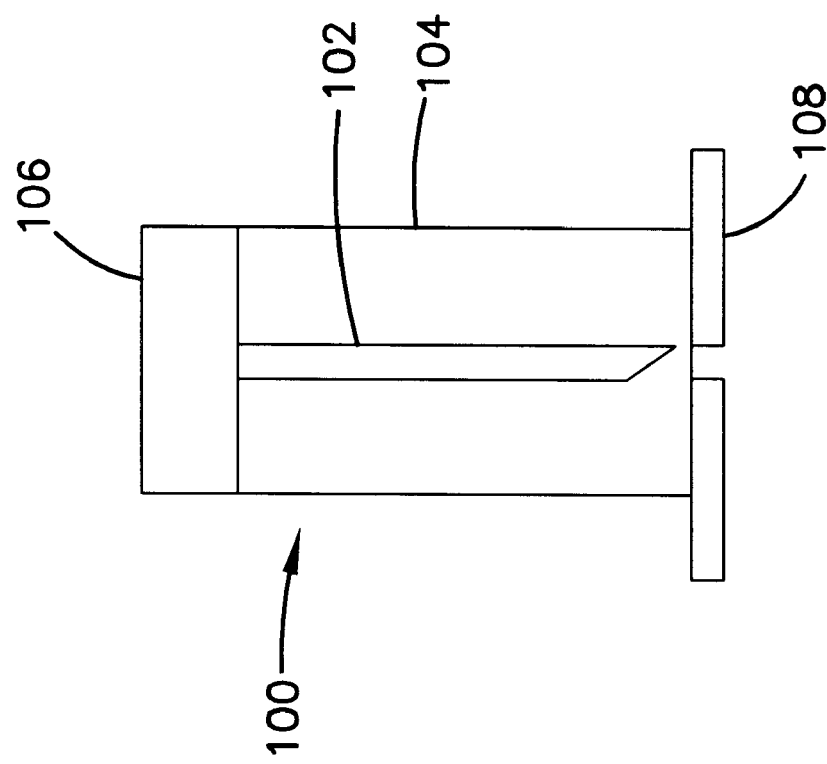
FIG. 6 is a schematic cross-sectional view of another embodiment of a reusable skin-piercing device, according to the present invention.

FIGS. 6 and 7 schematically illustrate another embodiment of a reusable skin-piercing device 100. This device 100 includes a skin-piercing element 102 and a sleeve 104 disposed in a housing (not shown). The skin-piercing element 102 can be formed using any of the ceramic materials described above or using a hard metallic material (e.g., a material that includes tungsten, tantalum, molybdenum, or compounds of these elements) that retains sufficient sharpness when used for multiple piercing events. The skin-piercing element 102 of this embodiment does not require the resistive region of the previously-described embodiments.

The sleeve 104 is typically formed of an elastomeric material with a sterilizing agent embedded, dissolved, suspended, or coated on or in the elastomeric material. An elastomeric material is typically selected to be compressible and compatible with the selected sterilizing agent. Examples of suitable elastomeric materials include silicone rubbers, polyisoprenes, polybutadiene-polystyrene copolymers, polychloroprenes, and polybutadiene-polystyrene-polyacrylonitrile copolymers. The elastomeric material is optionally crosslinked (e.g., vulcanized) to increase hardness or durability.

The sterilizing agent can be selected from those known in the art. Examples of types of suitable sterilizing agents include oxidants, phenols, epoxides, peroxides, polymers of formaldehyde and other mono-, di-, and polyaldehydes (e.g. glutaraldehyde), hydrogen peroxide evolving systems, iodine-containing complexes, and metal salts of silver or copper. Specific examples include peroxiacetic acid, peroxibenzoic acid, chloramine-T, brominated phenols or quinones (e.g., tetrabromobenzoquinone), iodine-polymer complexes such as a complex of iodine with polyvinylpyridine, potassium triiodide, and tetraalkyl ammonium triiodide. Other suitable chemical sterilizers are described in, for example, U.S. Pat. Nos. 4,305,905; 4,448,750; 4,738,840; 5,403,549; 5,637,307; and 5,756,090, all of which are incorporated herein by reference.

One example of a hydrogen peroxide evolving system includes a peroxide-generating enzyme, such as an oxidase (e.g., glucose oxidase or lactate oxidase). The peroxide-generating enzyme is preferably thermostable or disposed in a sol-gel matrix to make the enzyme thermostable, as described, for example, in U.S. Pat. No. 5,972,199 and PCT Patent Application Publication No. WO 98/35053, both of which are incorporated herein by reference. The peroxide-generating enzyme is disposed in the proximity of the skin-piercing element. The substrate (e.g., glucose for glucose oxidase or lactate for lactate oxidase) of the peroxide-generating enzyme is provided in a container disposed in the housing of the skin-piercing device. Prior to the initial use of the device, the container is opened to allow the substrate to come into contact with the peroxide-generating enzyme. This results in the, typically, continuous production of hydrogen peroxide to sterilize the skin-piercing element. An antibiotic agent can be provided with the substrate, if desired. Optionally, a peroxidase enzyme (preferably, a thermostable peroxidase, such as soybean peroxidase) is included with the peroxide-generating enzyme. Hydrogen peroxide in combination with the peroxidase enzyme form free radicals or other species that can also be effective in sterilization.

The sterilizing agent is provided in an effective amount to be used for a desired number of skin-piercing events. Selection of an amount of the sterilizing agent can account for factors, such as, for example, evaporation of other loss of sterilizing agent during manufacture, packaging, storage, and use.

In operation, a load 106 pushes the skin-piercing element 102 through the sleeve 104 and out an opening in a wall 108 of a housing of the device 100. The elastomeric material of the sleeve 104 is compressible, as illustrated in FIGS. 6 and 7. Before and after the piercing operation, the skin-piercing element 102 is in contact with the sterilizing agent in the sleeve 104 to deactivate or eliminate pathogens. The compression of the elastomeric material of the sleeve 104 optionally provides more intimate contact between the skin-piercing element 102 and the sterilizing agent. The sleeve 104 typically has an opening through which the skin-piercing element 102 extends, however, in some embodiments, the initial use of the device 100 includes pushing the skin-piercing element 102 through a solid sleeve 104 to form an opening.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

We claim:

1. A method of collecting a blood sample, the method comprising:
    providing a skin-piercing device comprising a housing, a ceramic blade movable into and out from the housing, and a resistive region in thermal contact with the blade;
    sterilizing the skin-piercing device by:
        (a) passing a current through the resistive region, and
        (b) heating the blade;
    piercing a skin of a patient, and
    collecting a blood sample after piercing the skin.

2. The method of claim 1, wherein the step of collecting a blood sample comprises:
    collecting a blood sample of less than 5 $\mu$L.

3. The method of claim 1, wherein the method further comprises:
    after collecting the blood sample, again sterilizing the skin-piercing device.

4. A method of collecting a blood sample, the method comprising:
    providing a skin-piercing device comprising:
        (a) a ceramic blade, and
        (b) a resistive region in thermal contact with the blade;
    sterilizing the skin-piercing device by:
        (a) passing a current through the resistive region,
        (b) heating the blade, and
        (c) then cooling the blade;
    piercing a skin of a patient with the cooled blade, and
    collecting a blood sample after piercing the skin.

5. The method of claim 4, wherein the step of collecting a blood sample comprises:
    collecting a blood sample of less than 5 $\mu$L.

6. The method of claim 4, the method further comprises:
    after collecting the blood sample, again sterilizing the skin-piercing device.

7. The method of claim 4, wherein the method comprises:
    providing a skin-piercing device comprising at least two conductors spaced apart from each other and configured and arranged for contact with the resistive region.

* * * * *

UNITED STATES PATENT AND TRADEMARK OFFICE
CERTIFICATE OF CORRECTION

PATENT NO.    : 6,623,501 B2
DATED         : September 23, 2003
INVENTOR(S)   : Heller et al.

It is certified that error appears in the above-identified patent and that said Letters Patent is hereby corrected as shown below:

<u>Column 8,</u>
Line 34, "claim 4, the method" should read -- claim 4, wherein the method --

Signed and Sealed this

Twentieth Day of January, 2004

JON W. DUDAS
*Acting Director of the United States Patent and Trademark Office*